United States Patent [19]
Busch et al.

[11] Patent Number: 5,291,905
[45] Date of Patent: Mar. 8, 1994

[54] HAIR TREATMENT APPLICATOR

[75] Inventors: Peter Busch, Erkrath; Klaus Thiele, Langenfeld; Horst Hoeffkes, Duesseldorf-Hellerhof, all of Fed. Rep. of Germany

[73] Assignee: Henkel Kommanditgesellschaft auf Aktien, Duesseldorf-Holthausen, Fed. Rep. of Germany

[21] Appl. No.: 924,387

[22] PCT Filed: Mar. 13, 1989

[86] PCT No.: PCT/EP89/00262
§ 371 Date: Sep. 21, 1990
§ 102(e) Date: Sep. 21, 1990

[87] PCT Pub. No.: WO89/09002
PCT Pub. Date: Oct. 5, 1989

Related U.S. Application Data

[63] Continuation of Ser. No. 573,226, Sep. 21, 1990, abandoned.

[30] Foreign Application Priority Data

Mar. 22, 1988 [DE] Fed. Rep. of Germany ....... 3809498
Dec. 14, 1988 [DE] Fed. Rep. of Germany ....... 3842006

[51] Int. Cl.⁵ .......................................... A45D 24/22
[52] U.S. Cl. .................................... 132/116; 132/114; 132/202; 424/70; 424/71; 401/283
[58] Field of Search ............... 132/202, 203, 207, 208, 132/108, 109, 112, 113, 114, 116, 120; 424/70, 71; 401/198, 199, 201, 283

[56] References Cited

U.S. PATENT DOCUMENTS

| | | | |
|---|---|---|---|
| 2,463,611 | 3/1949 | Green et al. | 132/108 |
| 3,100,179 | 8/1963 | Perry | 424/71 |
| 3,155,591 | 11/1964 | Hilfer | 424/70 |
| 3,530,215 | 9/1970 | Greif et al. | 424/71 |
| 3,840,338 | 10/1974 | Zviak et al. | 424/71 |
| 3,861,407 | 1/1975 | Gabriele | 132/108 |
| 4,187,289 | 2/1980 | Eckhardt | 424/70 |
| 4,361,157 | 11/1982 | James | 132/204 |
| 4,579,131 | 4/1986 | Syed | 132/202 |
| 4,585,018 | 4/1986 | O'Connor | 132/120 |
| 4,588,760 | 5/1986 | Jaehowicz et al. | 132/202 |
| 4,767,618 | 8/1988 | Grollier et al. | 424/70 |
| 4,770,873 | 9/1988 | Wolfram et al. | 424/70 |
| 4,796,646 | 1/1989 | Grollier et al. | 132/202 |
| 4,867,183 | 9/1989 | Busch et al. | 132/114 |
| 4,913,900 | 4/1990 | Kolc et al. | 132/204 |
| 4,993,437 | 2/1991 | Kimura et al. | 132/112 |

FOREIGN PATENT DOCUMENTS 0097322 1/1984 European Pat. Off. ............ 401/283

Primary Examiner—Gene Mancene
Assistant Examiner—Frank A. LaViola
Attorney, Agent, or Firm—Wayne C. Jaeschke; Norvell E. Wisdom, Jr.; Henry E. Millson, Jr.

[57] ABSTRACT

An applicator consisting of a dispenser in the form of a comb or brush and an active-substance preparation containing at least one hair-softening or hair-setting component in a concentration of from 0.01 to 20% by weight, based on the total weight of the active-substance preparation, and having a viscosity at room temperature of from 0.9 to 12 mPa.s enables hair to be specifically aftertreated with minimal effort and without adversely affecting the hair or scalp.

20 Claims, 1 Drawing Sheet

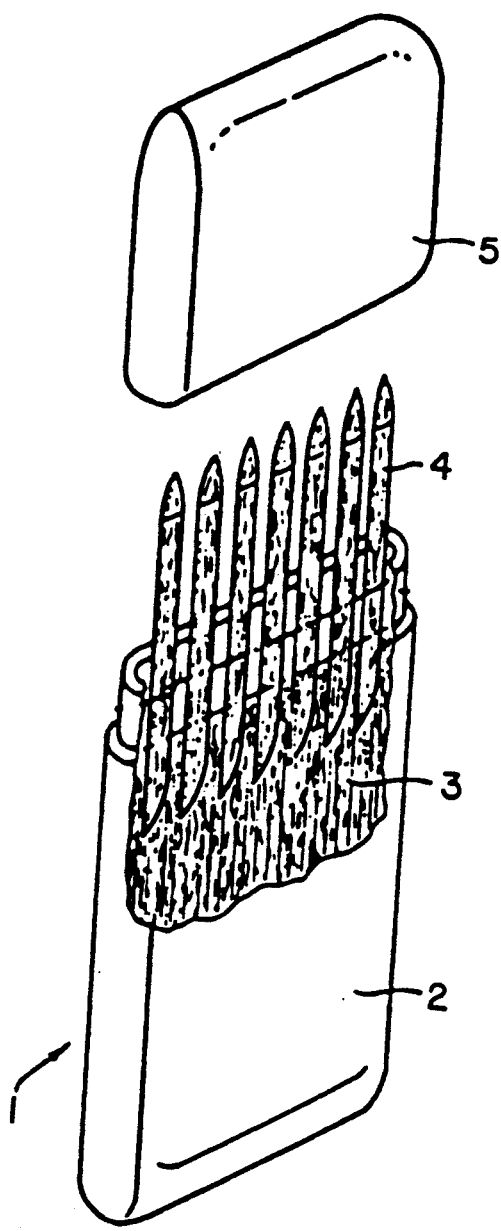

HAIR TREATMENT APPLICATOR

This application is continuation of Ser. No. 07/573,226 Sep. 21, 1990 now abandoned.

This invention relates to applicators for the treatment of hair consisting of a dispenser in the form of a comb or brush and an active-substance preparation for the care, softening or setting of hair.

In addition to the desired effects, many forms of hair treatment, in which active substances are applied to the hair, also result in serious stressing of, or damage to, the hair. Accordingly, it is advisable, for example after permanent wave treatment or dyeing of the hair, to subject the hair to an aftertreatment. The softening, conditioning and/or setting preparations applied to the hair in this aftertreatment are intended to prevent permanent damage to the hair and to provide it with other desirable properties including, for example, good wet and dry combability, longer holding of styles and protection against damp air.

Conventional aftertreatments are rinses, in which the active substances are applied to the hair, for example, in the form of a solution, a dispersion, a cream or an emulsion. After a certain contact time, the hair is then rinsed and subsequently dried. Accordingly, aftertreatments of this type involve considerable effort and, in many cases, also result in further unwanted adverse stressing of the scalp. In addition, quick-drying resin solutions generally formulated as hair sprays are used to protect hairstyles against moisture and to improve their hold. In this case, too, more controlled application of the active substances to the hair and avoiding the problem of propellents involved in the formulation of sprays would be an advantage.

Accordingly, there is a need for a simple hair aftertreatment process which has little or no ill-effect on the scalp. In addition, it would be of advantage to be able specifically to aftertreat individual, particularly stressed regions of the hair.

It is known that the hair as a whole or individual hair strands can be colored by means of a dispenser, for example in the form of a comb or brush, with minimal effort and without affecting the scalp. Dispensers of the type in question, which also dispense a liquid, for example a hair dye, during combing or brushing of the hair, are described, for example, in DE-OSS 27 49 074 and 36 22 234 and in DE-GbM 79 32 856. Another dispenser is described in Applicants, German patent application 38 09 498.

The dispensers consist in principle of a storage vessel for the liquid to be applied which communicates through connecting passages with the teeth or bristles through which the liquid is dispensed. This storage vessel may be mounted on the comb or the brush or, for example, may be integrated with its handle or spine. The dispensers may be both rigid and, if desired, equipped with a vibration mechanism to promote dispensing of the liquid.

It has now been found that dispensers show particularly advantageous properties in combination with certain hair-softening and/or setting active-substance preparations.

Accordingly, the present invention relates to a hair treatment applicator consisting of a dispenser in the form of a comb or a brush and an active-substance preparation which contains at least one hair-softening or hair-setting component, characterized in that the hair-softening and/or hair-setting components are present in a concentration of from 0.01 to 20% by weight, based on the total weight of the active-substance preparation, and in that the active-substance preparation has a viscosity at room temperature of from 0.9 to 12 mPa.s.

Combs or brushes of the type mentioned above may be used as the dispenser. The dispenser according to German patent application 38 09 498 is preferred and is illustrated in the sole drawing figure, which is a perspective view, partially broken away, of one embodiment of this type of dispenser. This dispenser 1 consists of a reservoir 3 for the active-substance preparation of a first porous material within a housing 2 and teeth 4 of a second porous material inserted into, and in capillary communication with, the first porous material, the teeth being formed with closed pores in the surface region of their free ends and the main pore direction both of the second porous material of the teeth and of the first porous material of the reservoir being substantially parallel to the longitudinal axis of the teeth, the first porous material of the reservoir extending over several times the depth of penetration of the teeth in the penetration direction. A cap 5 is placed over the teeth 4 when the dispenser is not in use, to prevent drying of the liquid within the teeth and reservoir.

So far as the details of this dispenser are concerned, reference is specifically made to the disclosure of the cited patent application.

The dispenser may be in the form of a non-reuseable product which is discarded after the supply of active-substance preparation has been used up. However, it is preferred to design the dispenser in such a way that it may be refilled with the active-substance preparation and is therefore suitable for permanent use.

The active-substance preparation preferably contains concentrations of hair-softening and/or hair-setting components of from 0.01 to 10% by weight and more especially from 0.01 to 5% by weight, based on the total weight of the active-substance preparation.

The active-substance preparation may be formulated, for example, as a solution, dispersion or emulsion. Suitable solvents or dispersants are, for example, water, lower alcohols and other organic compounds tolerated by the skin. According to the invention, the active-substance preparation is preferably formulated as an aqueous solution or emulsion.

The preparation intended for the dispenser must exhibit certain rheologic properties. To ensure the release of an adequate quantity of active substance in use, the viscosity of the active-substance preparation should not be too high. On the other hand, the viscosity must have a certain minimum value to prevent unwanted and uncontrolled outflow of the active-substance preparation. Accordingly, the active-substance preparations should be adjusted to a viscosity of from about 0.9 to 12 mPa.s at room temperature. According to the invention, viscosities of from about 0.9 to 6.5 mPa.s at room temperature are particularly preferred.

These viscosities may be determined, for example, by means of a Höppler falling-ball viscosimeter.

It has also been found to be of advantage for the active-substance preparations to have a surface tension of from 20 to 70 dyn/cm and more especially from 30 to 40 dyn/cm.

In addition, the components used in the preparations should not have too high a vapor pressure which, in the event of prolonged storage, could lead to a significant depletion of this component in the mixture and hence to changes, for example in rheologic behavior.

If the preparation is formulated as a solution, the active substances should be sufficiently soluble in the solvents selected to be able to be applied to the hair in the desired quantity. Accordingly, it is preferred to use hair-softening and hair-setting components which have a solubility of at least 0.1 g/l in the selected solvent, particularly water.

Preferred hair-softening active substances are quaternary ammonium compounds.

Suitable quaternary ammonium compounds are, for example, alkyl trimethyl ammonium salts containing 12 to 22 carbon atoms in the optionally substituted alkyl chain, such as for example hexadecyl trimethyl ammonium salts and ricinoleic acid propylamidotrimethyl ammonium salts, and dialkyl dimethyl ammonium salts containing 2 to 22 carbon atoms in the optionally substituted alkyl chain, such as for example 2-hydroxyhexadecyl-2-hydroxyethyl dimethyl ammonium salts, dodecylethyl dimethyl ammonium salts, stearylbenzyl dimethyl, dodecylbenzyl dimethyl and other alkylbenzyl dimethyl ammonium salts, distearyl dimethyl ammonium salts, lanolin fatty acid amidopropylethyl dimethyl ammonium salts, cetyl-2-hydroxyethyl dimethyl ammonium salts, dicoconut acyl dimethyl ammonium salts, dirapeseed oil acyl-1,1-dimethylethyl dimethyl ammonium salts, dioleic acid isopropyl ester dimethyl ammonium salts, gluconamidopropyl-2-hydroxyethyl dimethyl ammonium salts, minkamidopropyl-2-hydroxyethyl dimethyl ammonium salts. Other suitable quaternary ammonium compounds are polyoxyethyl stearyl ammonium salts, penta(oxyethylene) octadecyl ammonium salts, bis-tallow acyl aminoethyl-2-hydroxyethyl methyl ammonium salts, coconut pentaethoxymethyl ammonium salts, alkyl-3-acylaminoethyl imidazolinium salts, tallow alkyl amidoethyl methyl-2-tallow alkyl imidazolinium salts, bis-oleylamidoethyl-2-oleyl imidazolinium salts and alkylamidoethyl methyl alkyl imidazolinium salts. Compounds of the alkyl pyridinium salt type, such as lauryl pyridinium salts, are also suitable. The alkyl and acyl groups in the compounds mentioned normally contain about 12 to 22 carbon atoms. Suitable counterions in these salts are, for example, halide ions, particularly chloride and bromide ions, lactate ions, methosulfate ions, ethosulfate ions, phosphate ions, hydrogen and dihydrogen phosphate ions, saccharinate ions and acetate ions.

In addition, ampholytic and/or zwitterionic surfactants may be used as hair-softening components.

Zwitterionic surfactants are surface-active compounds which contain at least one quaternary ammonium group and at east one $-COO^{(-)}$ or $-SO_3^{(-)}$ group in the molecule. Particularly suitable zwitterionic surfactants are the so-call betaines, such as N-alkyl-N,N-dimethyl ammonium glycinates, for example coconut alkyl dimethyl ammonium glycinate, N-acylaminopropyl-N,N-dimethyl ammonium glycinates, for example coconut acylaminopropyl dimethyl ammonium glycinate, and 2-alkyl-3-carboxymethyl-3-hydroxyethyl imidazolines containing 8 to 18 carbon atoms in the alkyl or acyl group and also coconut acylaminoethyl hydroxyethyl carboxymethyl glycinate.

Ampholytic surfactants are surface-active compounds which, in addition to a $C_8$–$C_{18}$ alkyl or acyl group in the molecule, contain at least one free amino group and at least one $-COOH$ or $-SO_3H$ group and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing approximately 8 to 18 carbon atoms in the alkyl group.

A preferred group of hair-setting active substances are film-forming polymers.

Suitable substances are, for example, polyvinyl pyrrolidones and copolymers and terpolymers thereof with vinyl acetate and/or vinyl propionate (Luviskol ®, Nasuna ®), polybutyraldehyde acetals (Nasuna ®), quaternary polymers of the type formed by reaction of polyvinyl pyrrolidone with quaternary ammonium compounds (Gafquat ®), copolymers of methyl vinyl ether and maleic anhydride (Gantrez ®), copolymers of vinyl acetate and N-vinyl-5-methyl-2-oxazolidone (Devlex ®), mixtures of polyvinyl pyrrolidone, acrylate esters and (meth)acrylic acid (VEM ® resins), polyacrylates (Carboset ®), carboxylated vinyl acetate terpolymers (Resyn ®), amphoteric acrylate resins (Amphomer ®), polyglycol polyamine condensation resins (Polyquart ®), cationic quaternized celluloses (Polymer JR ®, Celquat ®) and polymeric dimethyl diallyl ammonium chloride and copolymers thereof with acrylamide (Merquat ®), providing they are sufficiently soluble in the base of the active-substance preparation, i.e. generally water, a suitable organic solvent or a corresponding aqueous mixture.

The preparations according to the invention may contain organic solvents, preferably in quantities of from 0.1 to 10% by weight, based on the active-substance preparation, more especially lower alcohols containing 1 to 4 carbon atoms, such as for example ethanol, 1-propanol, isopropanol, ethylene glycol, glycerol or butanol. Ethanol and isopropanol are preferred organic solvents.

If desired, the active-substance preparations according to the invention may contain as further components anionic, cationic and/or nonionic surfactants, oil components, biogenic active substances, such as lecithin, tocopherols, vegetable extracts, proteins and protein hydrolyzates, super-fatting agents, such as polyol fatty acid esters, perfumes and pH regulators.

The pH value of the active-substance preparations according to the invention is in the range from 2 to 10, preferably in the range from 5 to 8 and more preferably in the range from 5 to 7. Organic acids, such as for example citric acid, or ammonia may be used to establish the desired pH value. It can be of advantage to formulate pH-buffered active-substance preparations by addition of corresponding salts, for example sodium citrate, ammonium chloride, ammonium sulfate or ammonium carbonate.

The present invention also relates to the use of the applicator claimed in any of claims 1 to 8 for the treatment of hair.

The softening treatment of the hair carried out as described above is extremely simple and may be carried out, for example, without any complicated wet operations or subsequent drying. The softening product may also be specifically applied, for example to regions particularly endangered by split ends.

The formulations of the active-substance preparations may often be confined to a few constituents, so that the invention affords advantages over conventional wet processes in this regard, too.

The following Examples are intended to illustrate the invention without limiting it in any way.

EXAMPLES

1. Formulations

The following active-substance preparations were used in a dispenser according to German patent application 38 09 8:

| Preparation | Components | |
|---|---|---|
| A | Dehyquart ® A[1] | 5% by weight (based on active substance) |
| | water | ad 100% by weight |
| B | Dehyquart ® E[2] | 5% by weight (based on active substance) |
| | water | ad 100% by weight |
| C | Dehyton ® AB 30[3] | 5% by weight (based on active substance |
| | N-stearyl-N,N-dimethyl ammonium glycinate | 2.5% by weight (based on active substance |
| | water | ad 100% by weight |
| D | Dehquart ® A | 5% by weight (based on active substance) |
| | Phospholipone-100[4] | 5% by weight (based on active substance) |
| | water | ad 100% by weight |
| E | Dehyquart ® A | 5% by weight (based on active substance) |
| | Cetiol ® HE[5] | 5% by weight (based on active substance) |
| | water | ad 100% by weight |

[1]Trimethyl hexadecyl ammonium chloride (35% active substance in water) (HENKEL)
[2]Dimethyl-N-(2-hydroxyethyl)-N-(2-hydroxyhexadecyl)-ammonium chloride (approx. 27% active substance in water) (HENKEL)
[3]Fatty amine derivative of betaine structure, CTFA name: Coco-Betaine (approx. 30% active substance and 6% NaCl in water) (HENKEL)
[4]Lecithin (NATTERMANN)
[5]Polyol fatty acid ester (HENKEL)

2. Determination of wet and dry combability:

To determine the wet and dry combability of hair treated with the applicator according to the invention, twenty 11 cm long strands of brown European hair weighing 0.8 g were cleaned under defined conditions by treatment with a salt solution, an alcoholic solution and an anionic surfactant solution The hair strands were then thoroughly rinsed with water at 30° C., the water stripped off and the strands of hair subsequently dried for 5 hours at 30° C./40% relative air humidity To determine dry combability, the strands of hair were then treated with the applicator according to the invention which was drawn through the hair strands twenty times The combing resistance, i.e. the force required to draw a comb through the strands of hair, was then measured. To reduce the measurement error, the determination was carried out 15 times and the work integrals averaged. The measurement was performed in a tensile testing machine in which the strands of hair were combed by two combs arranged scissor-fashion. To prevent the strands of hair being combed at the same place during further combings, the comb system can be turned about an axis. The measured values are directly evaluated by a linked computer.

The improvement (or deterioration) in dry combability was defined as $$DC = \frac{\text{work integral for treated hair}}{\text{comparison value}} \cdot 100\%$$

The comparison value was the work integral determined during measurement of the combing resistance of the cleaned hair rinsed with water and dried, but not treated with the applicator according to the invention.

To determine wet combability, the strands of hair were placed under defined conditions in a wet state after after analogous treatment with the applicator according to the invention. This was done in an apparatus consisting of a tank, a comb system and a thin water supply pipe. The comb system consisted of two combs of which the spines, offset through 180°, were spring-mounted on a rotatable roller and in each of which half the teeth were separated by wide intervals and half by narrow intervals. It was thus possible to place the strands of hair in a definitely preordered, wet state. Further particulars of this arrangement can be found in an Article by the inventors in the journal "Ärztliche Kosmetologie" which is presently in print.

The improvement (or deterioration) in wet combability was analogously defined as $$WC = \frac{\text{work integral for treated hair}}{\text{comparison value}} \cdot 100\%$$

The comparison value was the work integral determined during measurement of the combing resistance of the cleaned hair rinsed with water, dried and placed in a wet state under defined conditions, but not treated with the applicator according to the invention.

The results are shown in the following Table:

| Preparation | DC [%] | WC [%] |
|---|---|---|
| A | 22 | 56 |
| B | 64 | 34 |
| C | 37 | 38 |
| D | 23 | 37 |
| E | 44 | 35 |

The results show the considerable improvement in the wet and dry combability of hair which is obtained by using the applicator according to the invention.

What is claimed is:

1. An applicator for the treatment of hair, said applicator comprising:
   (A) a dispenser for contacting the hair;
   (B) a fluid treating composition having a viscosity at room temperature of from about 0.9 to about 12 mPa.s and comprising from about 0.01 to about 20% by weight, based on the total weight of the treating composition, of materials selected from the group of hair-softening and hair-setting components;
   (C) means for containing the fluid treating composition within the applicator; and
   (D) means for achieving transfer of the fluid treating composition from the applicator to the hair at a suitable rate for hair treatment when the applicator is contacted with the hair.

2. An applicator as claimed in claim 1, wherein the dispenser includes (i) a reservoir for the fluid treating composition of a first porous material within a housing and (ii) teeth of a second porous material inserted into, and in capillary communication with, the first porous material; the teeth having closed pores in the surface region of their free ends and the main pore direction both of the second porous material of the teeth and of the first porous material of the reservoir being substantially parallel to the longitudinal axis of the teeth, the first porous material of the reservoir extending over several times the depth of penetration of the teeth in the penetration direction.

3. An applicator as claimed in claim 2, wherein the fluid treating composition has a surface tension of from about 20 to about 70 dynes/cm.

4. An applicator as claimed in claim 3, wherein the surface tension of the fluid treating composition is from about 30 to about 40 dynes/cm.

5. An applicator as claimed in claim 2, wherein the fluid treating composition is an aqueous solution or emulsion.

6. An applicator as claimed in claim 5, wherein the fluid treating composition contains a hair-softening component having a solubility of at least about 0.1 g/l in water.

7. An applicator as claimed in claim 2, wherein the fluid treating composition contains a quaternary ammonium compound as a hair-softening component.

8. An applicator as claimed in claim 2, wherein the fluid treating composition contains a film-forming polymer as a hair-setting component.

9. An applicator as claimed in claim 2, wherein the fluid treating composition contains an organic solvent.

10. An applicator as claimed in claim 1, wherein the fluid treating composition has a surface tension of from about 20 to about 70 dynes/cm.

11. An applicator as claimed in claim 10, wherein the surface tension of the fluid treating composition is from about 30 to about 40 dynes/cm.

12. An applicator as claimed in claim 11, wherein the fluid treating composition contains an organic solvent.

13. An applicator as claimed in claim 1, wherein the fluid treating composition is an aqueous solution or emulsion.

14. An applicator as claimed in claim 13, wherein the fluid treating composition contains a hair-softening component having a solubility of at least about 0.1 g/l in water.

15. An applicator as claimed in claim 14, wherein the fluid treating composition contains a quaternary ammonium compound as a hair-softening component.

16. An applicator as claimed in claim 15, wherein the fluid treating composition contains a film-forming polymer as a hair-setting component.

17. An applicator as claimed in claim 1, wherein the fluid treating composition contains a quaternary ammonium compound as a hair-softening component.

18. An applicator as claimed in claim 1, wherein the fluid treating composition contains a film-forming polymer as a hair-setting component.

19. An applicator as claimed in claim 1, wherein the fluid treating composition contains an organic solvent.

20. A method of treating hair, comprising contacting the hair with an applicator comprising:
(A) a dispenser for contacting the hair;
(B) a fluid treating composition having a viscosity at room temperature of from about 0.9 to about 12 mPa.s and comprising from about 0.01 to about 20% by weight, based on the total weight of the treating composition, of materials selected from the group of hair-softening and hair-setting components;
(C) means for containing the fluid treating composition within the applicator; and
(D) means for achieving transfer of the fluid treating composition from the applicator to the hair at a suitable rate for hair treatment when the applicator is contacted with the hair.

* * * * *